United States Patent
Kim et al.

(10) Patent No.: US 10,788,489 B2
(45) Date of Patent: Sep. 29, 2020

(54) METHOD FOR DETECTION OF PROTEIN COMPRISING HISTIDINE-TAG USING IMMUNOCHROMATOGRAPHY

(71) Applicant: Daegu Gyeongbuk Institute of Science and Technology, Daegu (KR)

(72) Inventors: Eun Joo Kim, Daegu (KR); Won Bae Jeon, Daegu (KR); Sung Jun Lee, Daegu (KR); Se Geun Lee, Daegu (KR); Eun Sook Choi, Daegu (KR)

(73) Assignee: Daegu Gyeongbuk Institute of Science and Technology (KR)

( * ) Notice: Subject to any disclaimer, the term of this patent is extended or adjusted under 35 U.S.C. 154(b) by 659 days.

(21) Appl. No.: 14/930,718

(22) Filed: Nov. 3, 2015

(65) Prior Publication Data
US 2016/0131644 A1 May 12, 2016

(30) Foreign Application Priority Data
Nov. 7, 2014 (KR) .................... 10-2014-0154537

(51) Int. Cl.
*G01N 33/558* (2006.01)
*G01N 33/543* (2006.01)
*G01N 21/78* (2006.01)
*C07K 16/44* (2006.01)
*G01N 21/77* (2006.01)

(52) U.S. Cl.
CPC ............ *G01N 33/558* (2013.01); *C07K 16/44* (2013.01); *G01N 21/78* (2013.01); *G01N 33/54346* (2013.01); *G01N 33/54366* (2013.01); *G01N 2021/7759* (2013.01)

(58) Field of Classification Search
None
See application file for complete search history.

(56) References Cited

U.S. PATENT DOCUMENTS

| 2005/0277163 A1* | 12/2005 | Cheng .................. G01N 33/558 435/7.32 |
| 2012/0220049 A1* | 8/2012 | Bunce .................. G01N 33/558 436/501 |
| 2014/0093865 A1* | 4/2014 | Espinosa .............. G01N 33/558 435/5 |

FOREIGN PATENT DOCUMENTS

| JP | 2013040912 A | * | 2/2013 |
| KR | 1020090062121 A | | 6/2009 |
| KR | 1020100098221 A | | 9/2010 |

OTHER PUBLICATIONS

Cheng et al. as applied to claim 13 above, and further in view of Sakurai et al., Multi-colored immunochromatography using nanobeads for rapid and sensitive typing of seasonal influenza virus, Journal of Virological Methods, 209, (2014), p. 62-68 (published only Sep. 10, 2014) (Year: 2014).*
Cayman, His-Express Detection EIA Kit, Item No. 10012445, Cayman Chemical Company, Jul. 16, 2014 (15 pages) (Year: 2014).*
English abstract for KR 1020090062121 A (2009).
English abstract for KR 1020100098221 A (2010).

* cited by examiner

*Primary Examiner* — Ellen J Marcsisin
(74) *Attorney, Agent, or Firm* — Caesar Rivise, PC

(57) ABSTRACT

The present invention relates to a method for the detection of a protein including a histidine-tag using immunochromatography. The detection method of the present invention uses immunochromatography using the polymer particle fixed with the histidine-tag, wherein a histidine-tag specific antibody alone is used to detect a histidine-tag conjugated protein (recombinant protein) quickly without using a target protein specific antibody. This method is also efficient in detecting and quantifying the histidine-tagged protein included in the sample without using an additional apparatus but quickly and accurately.

16 Claims, 5 Drawing Sheets

Specification includes a Sequence Listing.

[Figure 1]
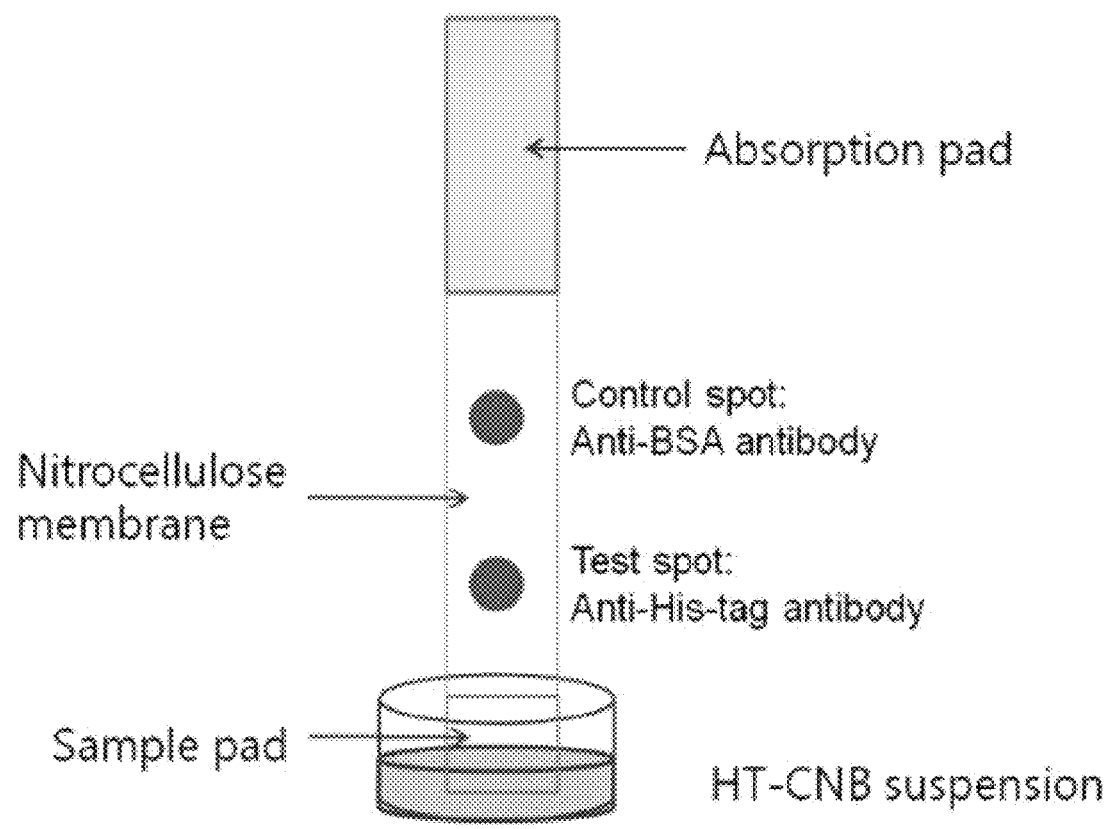

[Figure 2]
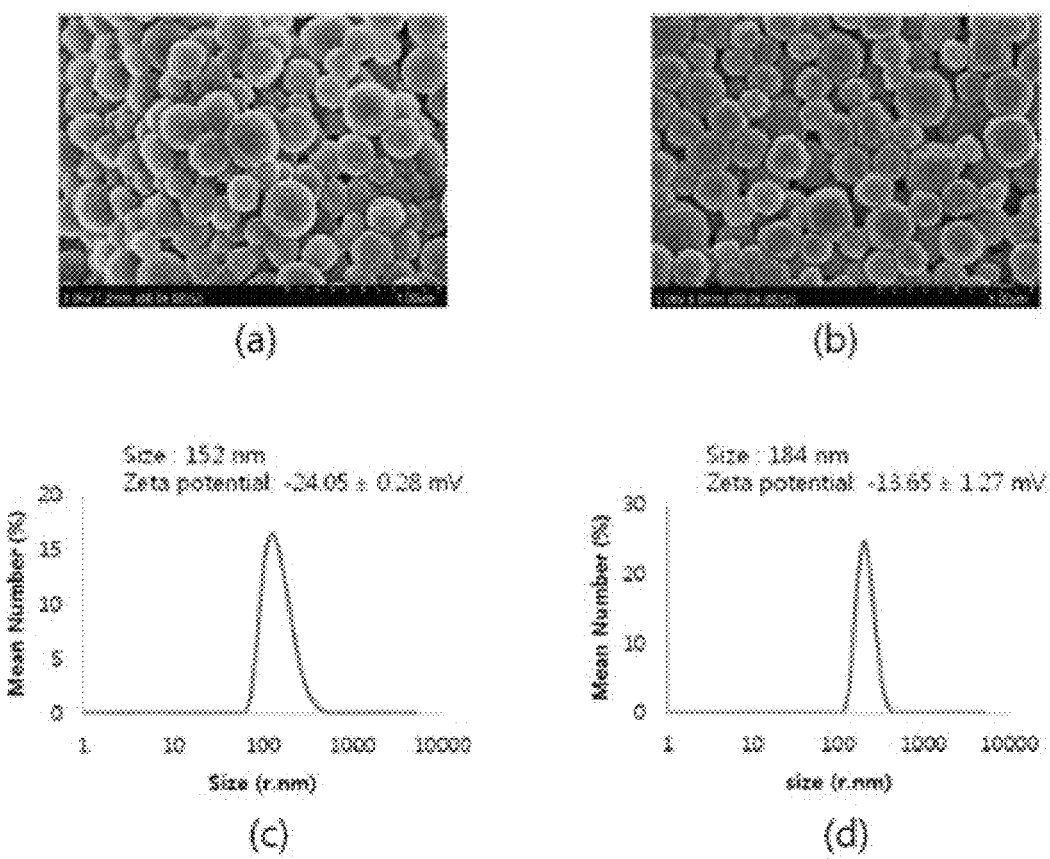

[Figure 3]
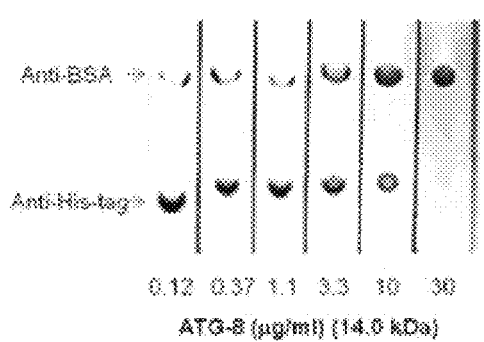
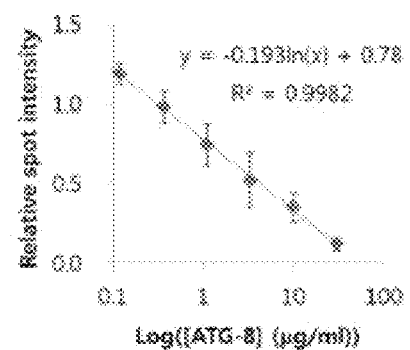
(a)        (b)

[Figure 4]
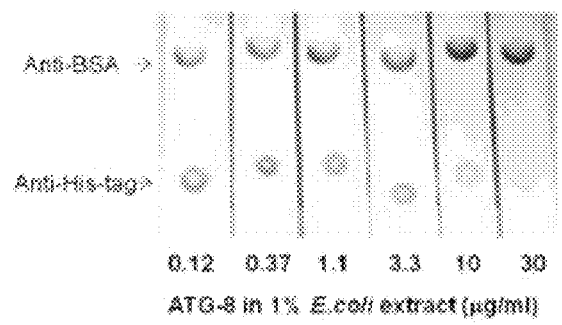
(a)
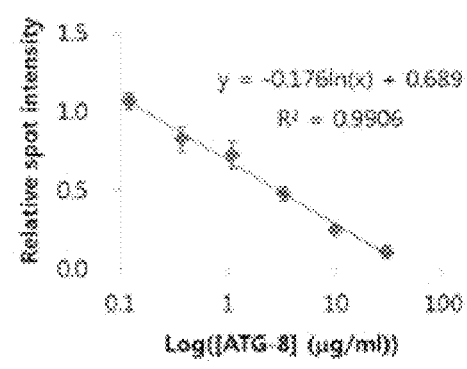
(b)

[Figure 5]
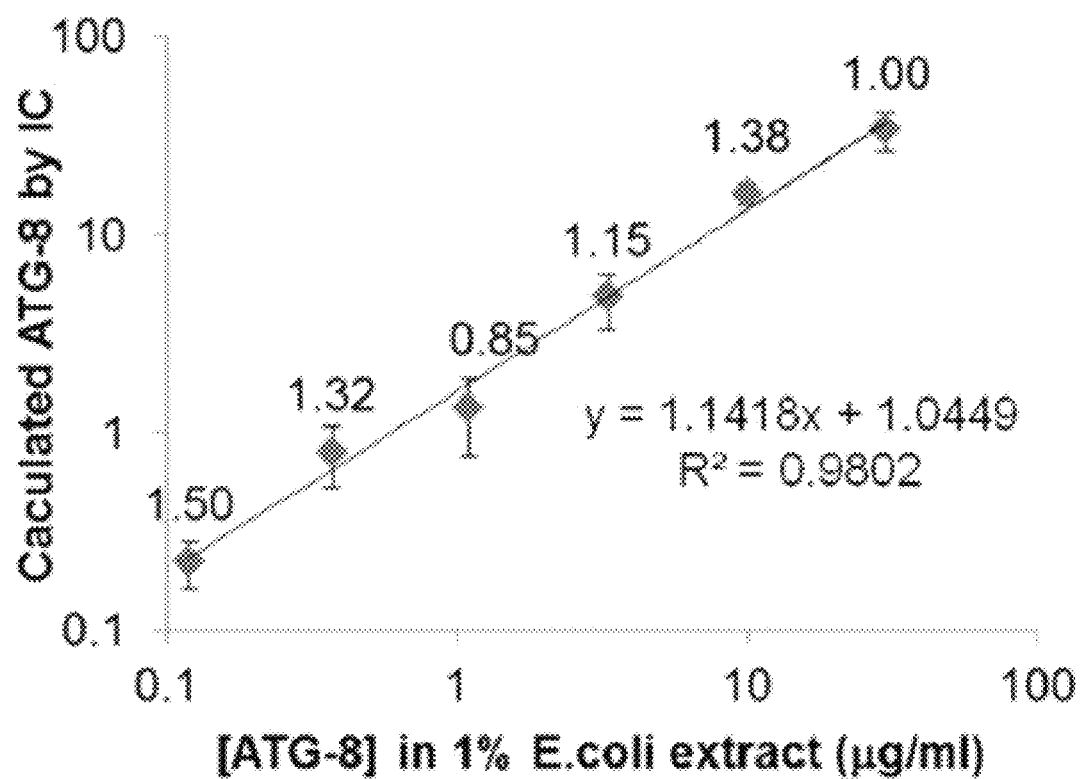

METHOD FOR DETECTION OF PROTEIN COMPRISING HISTIDINE-TAG USING IMMUNOCHROMATOGRAPHY

BACKGROUND OF THE INVENTION

1. Field of the Invention

The present invention relates to a method for the detection of a protein comprising histidine-tag using immunochromatography. More precisely, the invention relates to a method for detecting or quantifying a protein comprising histidine-tag included in a sample by performing immunochromatography using histidine-tagged nanoparticles.

2. Description of the Related Art

Histidine-tag is simply written as "histidine-tag". Histidine-tag is a short chain of sequential histidine residues which does not exist in a natural protein and is composed typically of 5~6 residues. It is conjugated to a protein by protein synthesis method specifically to one of amino acid chain terminals. The synthesized protein or peptide is then named as "tagged histidine" or "histidine-tagged protein". Histidine-tag binds strongly to such metals as nickel and cobalt by at least two histidine residues, and the histidine-tag protein can pass through the nickel- or cobalt-containing column. Histidine-tag is characterized by its strong bond to the column, so that it can be used as a marker protein that can be used for the separation of a target protein from a sample. So, histidine-tag is widely used for a protein and a peptide conjugation.

To detect the histidine-tagged protein (histidine labeled protein) with the conventional method, western blotting is performed or immunoprecipitation using a specific antibody that can be conjugated specifically to histidine-tag is performed before western blotting. However, this procedure of the prior art consumes time. Therefore, a detection method that uses metal particles for the fixation of such a protein as an antibody has been developed (Korean Patent Publication No. 2010-0098221). This detection method has a problem; which is that the characteristics and morphology of a target can be so easily changed according to the volume of a metal particle surface protein or the concentration of buffer. In the meantime, the detection method using immunochromatography does not change the characteristics or morphology of a target protein regardless of kinds or types of nanoparticles such as metal particles or polymer particles or the volume of a surface protein or the concentration of buffer. So, color change is not observed with any protein or buffer.

Korean Patent No. 0979463 describes a method for the detection of a target protein by using the specific bond of a histidine labeled protein with nickel in coupling with quantum dot. This method, however, is to detect the histidine labeled protein in cells or in organisms, indicating that it consumes time and is not simple to detect a target.

So, the present inventors tried to develop a novel method to detect accurately and easily the histidine-tagged protein or the histidine protein included in a sample. The present inventors first mixed the histidine-tagged nanoparticles with the sample containing the histidine-tagged protein or the histidine protein, and then performed immunochromatography using an immunochromatography strip loaded with a histidine-tag specific antibody.

As a result, the inventors confirmed that this method facilitated the detection of the histidine-tagged protein or the histidine protein included in a sample easily and accurately without using any additional apparatus, and also facilitated the quantification of the target protein, leading to the completion of the present invention.

SUMMARY OF THE INVENTION

This method is proposed to overcome the above mentioned problem of the prior art. Firstly, it is an object of the present invention to provide a method for the detection or quantification of the histidine-tagged protein or the histidine protein by using the nanoparticle having the histidine-tagged protein fixed thereon and immunochromatography.

Secondly, it is another object of the present invention to provide an immunochromatography kit for the detection or quantification of the histidine-tagged protein.

To achieve the first object of the invention, the present invention provides a method for the detection or quantification of the histidine-tagged protein containing the step of performing immunochromatography with the mixture of the nanoparticle having the histidine-tagged protein fixed thereon and the sample containing the histidine-tagged protein.

According to a preferred embodiment of the present invention, as stated in claim 1, the nanoparticle conjugated histidine-tagged protein has a histidine chain wherein 5~6 histidine residues are sequentially connected.

According to another preferred embodiment of the present invention, the nanoparticle is a metal particle or a polymer particle. At this time, the metal particle can be gold, silver, or white gold particle, and the polymer particle can be cellulose nanobead.

According to another preferred embodiment of the present invention, the size of the nanoparticle is 50~400 nm.

According to another preferred embodiment of the present invention, the nanoparticle conjugated histidine-tag competes with the histidine-tagged protein included in the sample in the course of immunochromatography.

According to another preferred embodiment of the present invention, the sample can be the cell extract expressing the histidine-tagged protein.

According to another preferred embodiment of the present invention, the method for the detection of the histidine-tagged protein is composed of the following steps:

(a) mixing the nanoparticle on which the histidine-tagged protein is fixed and the sample containing the histidine-tagged protein;

(b) performing immunochromatography with the above mixture using the immunochromatography strip on which the histidine-tag specific antibody is deposited; and (c) detecting the histidine-tagged protein by observing color development and measuring the strength of color development resulted from the conjugation reaction between the histidine-tag fixed on the nanoparticle and the histidine-tag specific antibody deposited on the immunochromatography strip.

According to another preferred embodiment of the present invention, when the histidine-tagged protein is included in the sample, the antibody conjugation reaction between the histidine-tag fixed on the nanoparticle and the histidine-tag specific antibody deposited on the immunochromatography strip is reduced, resulting in the decrease of the strength of color development in step (c) of the detection method.

On the contrary, when the histidine-tagged protein is not included in the sample, the antibody conjugation reaction between the histidine-tag fixed on the nanoparticle and the histidine-tag specific antibody deposited on the immunochromatography strip is increased, resulting in the increase of the strength of color development.

According to another preferred embodiment of the present invention, the method for the detection of the histidine-tagged protein is composed of the following steps:

(a) mixing the nanoparticle on which the histidine-tagged protein is fixed and the sample containing the histidine-tagged protein;

(b) performing immunochromatography with the above mixture using the immunochromatography strip on which the histidine-tag specific antibody is deposited; and (c) measuring the concentration of the histidine-tagged protein by measuring the strength of color development resulted from the conjugation reaction between the histidine-tag fixed on the nanoparticle and the histidine-tag specific antibody deposited on the immunochromatography strip.

According to another preferred embodiment of the present invention, in step (c) of the method, as the concentration of the histidine-tagged protein in the sample increases, the conjugation reaction between the histidine-tag fixed on the nanoparticle and the histidine-tag specific antibody deposited on the immunochromatography strip decreases, resulting in the decrease of the strength of color development.

As the concentration of the histidine-tagged protein decreases, the conjugation reaction between the histidine-tag fixed on the nanoparticle and the histidine-tag specific antibody deposited on the immunochromatography strip increases, resulting in the increase of the strength of color development.

According to another preferred embodiment of the present invention, in step (c) of the method, the standard quantification curve according to the concentration of the histidine-tagged protein was made in order to quantify the histidine-tagged protein included in the sample, and the protein comprising histidine-tag in the sample could be quantified by converting the color strength of the sample by referring the standard quantification curve.

To achieve the second object of the invention, the present invention provides an immunochromatography kit for the detection or quantification of a protein comprising histidine-tag, which comprises the immunochromatography strip composed of the sample pad to receive the liquid sample containing the target material, the measurement pad, and the absorption pad to absorb the liquid sample via capillary phenomenon; and the nanoparticle having histidine-tag fixed thereon.

According to a preferred embodiment of the present invention, the target material for the analysis can be a mixture of the nanoparticle having histidine-tag fixed thereon and the histidine-tagged protein, the target of the detection.

In a preferred embodiment of the present invention, the measurement pad can contain the test spot on which an anti-histidine-tag antibody is deposited, and the control spot on which an anti-BSA antibody is deposited in order to investigate the reaction induced by error.

In a preferred embodiment of the present invention, the kit can additionally contain an anti-histidine-tag antibody and an anti-BSA antibody.

In another preferred embodiment of the present invention, the measurement pad can be composed of a nitrocellulose membrane, and the absorption pad can be composed of a cellulose membrane.

ADVANTAGEOUS EFFECT

The method for the detection of a protein comprising histidine-tag using immunochromatography of the present invention can realize the fast detection of the histidine-tagged protein (recombinant protein) by using the histidine-tag specific antibody alone without any other target protein specific antibodies, and is efficient in fast and accurate quantification of the protein comprising histidine-tag included in a sample without any additional apparatus.

BRIEF DESCRIPTION OF THE DRAWINGS

The application of the preferred embodiments of the present invention is best understood with reference to the accompanying drawings, wherein:

FIG. 1 is a schematic diagram illustrating the method of immunochromatography using the nanoparticle on which histidine-tag is fixed.

FIG. 2 presents the photographs of images of the polymer particle (A) and the polymer particle having histidine-tag fixed thereon (B), used in this invention, and data of the size thereof (C).

FIG. 3 presents the photograph (A) illustrating the result of immunochromatography performed with the polymer particle having histidine-tag fixed thereon and PBS containing histidine-tag at different concentrations; and the standard graph (B) illustrating the color strength according to the concentration thereof.

FIG. 4 presents the photograph (A) illustrating the result of immunochromatography performed with the polymer particle having histidine-tag fixed thereon and 1% *E. coli* extract containing histidine-tag at different concentrations; and the standard graph (B) illustrating the color strength according to the concentration thereof.

FIG. 5 presents the schematized data obtained by comparing the results of FIG. 3B and FIG. 4B.

DESCRIPTION OF THE PREFERRED EMBODIMENTS

Hereinafter, the present invention is described in detail.

As explained hereinbefore, the conventional method for the detection of a protein comprising histidine-tag (histidine labeled protein) is Western blotting or immunoprecipitation using a histidine-tag specific antibody followed by Western blotting. However, these methods have a disadvantage of consuming a lot of time.

The present inventors tried to overcome the disadvantage of the conventional method by providing a method for the detection or quantification of a protein comprising histidine-tag using immunochromatography. This method enables fast detection of a protein comprising histidine-tag (recombinant protein) simply with a histidine-tag specific antibody and thus it is an effect of the present invention to provide a method for the fast and accurate detection or quantification of a protein comprising histidine-tag included in a sample without using an additional device.

Therefore, the present invention provides a method for the detection or quantification of a protein comprising histidine-tag containing the step of performing immunochromatography with the mixture of the nanoparticle on which the histidine-tagged protein is fixed and a sample containing the histidine-tagged protein.

In this invention, the histidine-tagged protein fixed on the nanoparticle can be a protein composed of 5~6 histidine residues which are sequentially connected.

The said 'histidine-tag' can be written as 'his-tag'. Histidine-tag is a short chain of sequential histidine residues which does not exist in a natural protein and is composed typically of 5~6 residues. Histidine-tag is generally conjugated to one of amino acid chain terminals via protein synthesis method. The synthesized protein or peptide is named as 'histidine-tagged protein', 'tagged histidine', or 'histidine-labeled protein'.

In this invention, the nanoparticle is a metal particle or a polymer particle. The metal particle herein is selected from the group consisting of silver, gold, and white gold particles. The polymer particle is preferably cellulose nanobead. However, the particle is not limited thereto and any metal particle or polymer particle that is known to those in the art can be used. For immunochromatography, any nanoparticle that can be combined with a specific antibody and accordingly efficient in developing color can be used without limitation.

The size of such a nanoparticle is 50~400 nm, and preferably 150~350 nm. If the size of the nanoparticle is smaller than 50 nm, the expansion speed of such nanoparticles is too fast to detect and measure the concentration of the histidine-tagged protein included in a sample because most of the histidine-tagged protein is combined with the anti-histidine tag antibody deposited on the immunochromatography strip. If the size of the nanoparticle is bigger than 400 nm, the expansion speed of such nanoparticles is too slow to detect and measure the histidine-tagged protein included in a sample because at this time the histidine-tagged protein is largely combined with the anti-histidine tag antibody deposited on the immunochromatography strip. Therefore, the size of nanoparticle is preferably determined by considering the molecular weight of the target histidine-tagged protein so as to match the expansion speed.

FIG. 2 of the present invention presents the photographs of images of the polymer particle (A) and the polymer particle having histidine-tag fixed thereon (B), used in this invention, and data of the size thereof (C). In a preferred embodiment of the present invention, cellulose nanobead was used as the polymer particle. The histidine-tagged protein ATG-8 was fixed on the surface of the cellulose nanobead, resulting in the preparation of the polymer particle on which histidine-tag is fixed.

The morphology and the size of the polymer particle prepared above were measured. As a result, as shown in FIG. 2A and FIG. 2B, the polymer particle showed a comparatively consistent round-shaped morphology. As shown in FIG. 2C and FIG. 2D, the radius of the polymer particle itself was approximately 152 nm, and the radius of the polymer particle having the histidine-tagged protein fixed thereon was approximately 184 nm, suggesting that the size of the polymer particle was increased because of the fixation of the histidine-tagged protein.

In the course of immunochromatography in this invention, the histidine-tag fixed on the nanoparticle competed with the histidine-tagged protein included in a sample.

The said sample can be a cell extract expressing a recombinant protein comprising histidine-tag, but not always limited thereto and any sample wanted to be detected or quantified for the histidine-tagged protein can be used. For example, in order to measure the purification efficiency of a recombinant protein comprising histidine-tag, immunochromatography of the invention can be performed with the purified product of the invention.

Particularly, the method for the detection of a protein comprising histidine-tag of the invention can be composed of the following steps:

(a) mixing the nanoparticle on which the histidine-tagged protein is fixed and the sample containing the histidine-tagged protein;

(b) performing immunochromatography with the above mixture using the immunochromatography strip on which the histidine-tag specific antibody is deposited; and (c) detecting the histidine-tagged protein by observing color development and measuring the strength of color development resulted from the conjugation reaction between the histidine-tag fixed on the nanoparticle and the histidine-tag specific antibody deposited on the immunochromatography strip.

The method for the detection of a protein comprising histidine-tag of the invention can be composed of the following steps:

(a) mixing the nanoparticle on which the histidine-tagged protein is fixed and the sample containing the histidine-tagged protein;

(b) performing immunochromatography with the above mixture using the immunochromatography strip on which the histidine-tag specific antibody is deposited; and (c) measuring the concentration of the histidine-tagged protein by measuring the strength of color development resulted from the conjugation reaction between the histidine-tag fixed on the nanoparticle and the histidine-tag specific antibody deposited on the immunochromatography strip.

The above procedure is illustrated in more detail step by step hereinafter.

First, step (a) is to mix the nanoparticle on which the histidine-tagged protein is fixed and the sample containing the histidine-tagged protein. In this invention, these two samples are mixed in order to induce competitive conjugation to the anti-histidine-tag antibody between the histidine-tagged protein fixed on the nanoparticle and the histidine-tagged protein included in the sample in the course of immunochromatography.

Secondly, step (b) is to perform immunochromatography with the above mixture using the immunochromatography strip on which the histidine-tag specific antibody is deposited.

In a preferred embodiment of the present invention, the immunochromatography strip was prepared in order to detect the histidine-tagged protein. Precisely, as shown in FIG. 1, cellulose membrane (absorption pad) and nitrocellulose membrane were put together to prepare the immunochromatography strip, followed by spotting with anti-histidine-tag polyclonal antibody and anti-BSA polyclonal antibody on the nitrocellulose membrane.

Lastly, step (c) is to detect or quantify the histidine-tagged protein by observing color development and measuring the strength of color development resulted from the conjugation reaction between the histidine-tag fixed on the nanoparticle and the histidine-tag specific antibody deposited on the immunochromatography strip.

As the concentration of the histidine-tagged protein in the sample increases, the conjugation reaction between the histidine-tag fixed on the nanoparticle and the histidine-tag specific antibody deposited on the immunochromatography strip decreases, resulting in the decrease of the strength of color development. In the meantime, as the concentration of the histidine-tagged protein decreases, the conjugation reaction between the histidine-tag fixed on the nanoparticle and the histidine-tag specific antibody deposited on the immunochromatography strip increases, resulting in the increase of the strength of color development. Thus, the histidine-tagged protein can be detected and quantified by the above observation.

In the quantification, the standard quantification curve according to the concentration of the histidine-tagged protein was made in order to quantify the histidine-tagged protein included in the sample, and the protein comprising histidine-tag in the sample could be quantified by converting the color strength of the sample by referring the standard quantification curve.

In a preferred embodiment of the present invention, to compare the color strength with the concentration of the histidine-tagged protein included in the sample, PBS containing the histidine-tagged protein (ATG-8) at different concentrations of 0.12, 0.37, 1.1, 3.3, 10, and 30 µg/ml was respectively prepared, followed by immunochromatography according to the method of the invention. Then, the strength of each spot at different concentrations was measured.

As shown in FIG. 3A, as the concentration of the histidine-tagged protein included in the solution increased, the conjugation reaction between the histidine-tagged protein fixed on the surface of the polymer particle and the anti-histidine-tag antibody spotted on the strip decreased, resulting in the decrease of color strength. From the standard quantification curve according to the concentration (FIG. 3B) was confirmed that the color strength decreased according to the concentration of the histidine-tagged protein included in the sample with presenting high correlation coefficient ($R^2$=0.9982).

In a preferred embodiment of the present invention, in order to confirm whether it is possible to detect or quantify the histidine-tagged protein included in a real cell extract, *E. coli* extract was mixed with the histidine-tagged protein (ATG-8), followed by immunochromatography.

As shown in FIG. 4A, as the concentration of the histidine-tagged protein included in the *E. coli* extract increased, the color strength on the spot having the anti-histidine-tag antibody fixed thereon was reduced. On the contrary, the color strength on the spot having the anti-BSA antibody fixed thereon increased. From the standard quantification curve according to the concentration (FIG. 4B) was confirmed that the color strength decreased according to the concentration of the histidine-tagged protein included in the sample with presenting high correlation coefficient ($R^2$=0.9906).

FIG. 5 presents the schematized data obtained by comparing the results of FIG. 3B and FIG. 4B. As shown in FIG. 5, the response value corresponding to the pure histidine-tagged protein of Example 2 indicates the slope of 1.1418, which was almost close to '1'.

In a preferred embodiment of the present invention, immunochromatography was performed using the polymer particle having the histidine-tagged protein fixed thereon, in order to confirm if the detection and quantification of a real recombinant protein comprising histidine-tag was possible with this method. To do so, fructose bisphosphate aldolase (FBA; Cusabio, USA) comprising histidine-tag and carbonic anhydrase I (CA-I, FBA; Cusabio, USA) comprising histidine-tag were added to the sample, followed by immunochromatography.

As a result, the color strength on the spot where the anti-histidine-tag antibody was fixed was reduced FBA/CA-I dose-dependently. As shown in Table 1, the concentration of the histidine-tagged protein included in the sample was measured by using the standard quantification curve of FIG. 5. As a result, FBA and CA-I dose-dependent reaction was confirmed even though there was difference in the actual concentrations of FBA and CA-I that had been added.

The above results indicate that immunochromatography using the nanoparticle was efficient not only in the detection of the histidine-tagged protein but also in the quantification of the concentration of the protein included in a sample. Thus, the present inventors confirmed that the method using immunochromatography realized in this invention was applicable to various histidine-tagged proteins, efficient in fast defection of the histidine-tagged protein (recombinant protein) only with an anti-histidine-tag antibody without using a target specific antibody separately, and efficient in easy but accurate quantification of the histidine-tagged protein included in a sample without using an additional device.

The present invention also provides an immunochromatography kit for the detection or quantification of a protein comprising histidine-tag, which comprises the immunochromatography strip composed of the sample pad to receive the liquid sample containing the target material, the measurement pad, and the absorption pad to absorb the liquid sample via capillary phenomenon; and the nanoparticle having histidine-tag fixed thereon.

The material of the immunochromatography strip can be a hydrophobic porous membrane such as nitrocellulose, nylon, and glass fiber, which can be penetrated by liquid materials. Also, the said measurement pad can include the test spot where the anti-histidine-tag antibody is deposited and the control spot where the anti-BSA antibody is deposited in order to detect error derived reaction (FIG. 1).

The measurement pad is preferably made of nitrocellulose, but not always limited thereto and any material that can accept the liquidity of the liquid sample for sparing enough time for the antigen/antibody reaction can be used. The absorption pad is not limited but has to be able to absorb the remaining materials after capillary phenomenon, which is preferably cellulose membrane.

The immunochromatography kit of the present invention contains the immunochromatography strip on which the antibody is deposited, or the anti-histidine-tag antibody and the anti-BSA antibody can be separately provided.

The target sample can be the mixture of the nanoparticle having histidine-tag fixed thereon, included in the immunochromatography kit for the detection or quantification of the histidine-tagged protein, and the sample containing the histidine-tagged protein, the target of detection.

When the liquid sample containing the target material is loaded on the sample pad, this sample moves through the medium via capillary phenomenon, beginning from the region where the sample was first dropped to the measurement pad. The target material continues to move by capillary phenomenon and then the histidine-tagged protein fixed on the nanoparticle competes with the histidine-tagged protein included in the sample for the conjugation with the anti-histidine-tag antibody deposited on the test spot of the measurement pad. If the histidine-tagged protein fixed on the nanoparticle is conjugated with the antibody, the conjugate cannot move through the medium anymore and remains on the measurement pad, by which the color is detected. If the histidine-tagged protein on the nanoparticle does not combine with the antibody, it continues to move further and then combines with the anti-BSA antibody deposited on the control spot with developing color thereon.

The protein comprising histidine-tag included in a sample hinders the antibody conjugation of the nanoparticle by combining competitively with the antibody of the test spot. At this time, the protein that has not been conjugated to the antibody of the test spot moves through the medium to the absorption pad.

So, if the histidine-tagged protein is included in the sample, the conjugation reaction of the histidine-tag fixed on the nanoparticle with the histidine-tag specific antibody deposited on the immunochromatography strip reduces, resulting in the decrease of the color strength. In the meantime, if the histidine-tagged protein is not included in the sample, the conjugation reaction of the histidine-tag fixed on the nanoparticle with the histidine-tag specific antibody deposited on the immunochromatography strip increases with presenting the color strength increased.

The present invention also provides a method for the detection or quantification of the histidine-tagged protein containing the step of performing immunochromatography with the mixture of the nanoparticle having the histidine-tagged protein fixed thereon and the sample containing the histidine-tagged protein.

In this method, the histidine-tagged protein specific antibody can be fixed on the nanoparticle instead of the histidine-tagged protein. At this time, the histidine-tag specific antibody fixed on the nanoparticle combines with the histidine-tagged protein included in the sample, resulting in the preparation of the antibody-nanoparticle complex that is specific to the histidine-tagged protein. When immunochromatography is performed, the histidine-tag specific antibody deposited on the immunochromatography strip is conjugated with the above complex to induce color development. At this time, as the concentration of the histidine-tagged protein in the sample increases, the color strength increases.

The present invention also provides a method for the detection or quantification of histidine containing the step of performing immunochromatography with the mixture of the nanoparticle having the histidine-tagged protein fixed thereon and the sample containing histidine.

The immunochromatography method using the nanoparticle of the present invention not only facilitates the detection of the histidine-tagged protein but also facilitates the measurement of the histidine concentration included in human blood, urine, and cerebrospinal fluid. By this measurement, such diseases related to the increase of histidine concentration as liver cirrhosis, renal disease, asthma, lung disease, and histidase deficiency can be confirmed.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Polymer Particle on Which Histidine-Tag Protein is Fixed

Cellulose nanobead (NanoAct™), the polymer particle, was purchased from DCN Diagnostics, and ATG8, the histidine-tagged protein for the fixation on the polymer particle surface, was purchased from Sino Biological Inc.

Hydrophobic interaction was used in order to fix the anti-histidine-tagged protein on the surface of the polymer particle. Precisely, the polymer nanobead was dispersed in PBS at the concentration of 0.01%, to which the histidine-tagged protein was added at the concentration of 0.5 µg/ml, followed by reaction for 30 minutes. To eliminate the non-reacted histidine-tagged protein remaining in the solution, centrifugation was performed at 5000 rpm. The Supernatant was eliminated and the remaining mixture was resuspended in PBS.

To prevent the random conjugation of other proteins on the surface of the polymer particle that did not have the histidine-tagged protein yet, BSA was added to the polymer nanobead resuspended in PBS at the concentration of 1%, followed by reaction for 30 minutes. To eliminate the non-reacted remaining BSA, centrifugation was performed at 5000 rpm and the supernatant was eliminated. The bead was then resuspended in PBS.

The morphology of the polymer particle prepared above was observed under scanning electron microscope (SEM), and the size of the polymer particle was measured by using dynamic light scattering (DLS) nanoparticle analyzer.

As a result, as shown in FIG. 2A and FIG. 2B, the polymer particle was confirmed to have a comparatively regular round shape. The radius of the polymer particle that did not combined with the histidine-tagged protein was about 152 nm, and the radius of the polymer particle on which the histidine-tagged protein was fixed was approximately 184 nm, suggesting that the size of the polymer particle was a little bit increased because of the histidine-tagged protein fixed thereon.

EXAMPLE 2

Immunochromatography Using the Polymer Particle Having the Histidine-Tagged Protein Fixed Thereon <2-1> Preparation of Immunochromatography Strip In order to detect a protein comprising histidine-tag, an immunochromatography strip was prepared. As shown in FIG. 1, cellulose membrane (absorption pad; 01006906, Bore Da Biotech, Korea) and nitrocellulose membrane (LFNC-C-SS04-10 um, Nupore Filtration Systems Pvt. Ltd., India) were put together to prepare the immunochromatography strip. The anti-histidine-tag polyclonal antibody (Bethyl Laboratories, Inc., USA) was spotted on the bottom of the nitrocellulose membrane. In the meantime, the anti-BSA (bovine serum albumin) polyclonal antibody (Bethyl Laboratories, Inc., USA) was spotted on the upper side of the nitrocellulose membrane for the reliability.

<2-2> Concentration Dependent Detection and Quantification of the Protein Comprising Histidine-Tag To compare the color strength according to the concentration of the histidine-tagged protein included in samples, immunochromatography was performed by using the immunochromatography strip prepared in Example <2-1>.

First, 30 µg/ml of the histidine-tagged protein (ATG-8) was added to PBS (Phosphate Buffered Saline) solution. 30 µg/ml of the histidine-tagged protein (ATG-8) was three-fold diluted serially to make each final concentration of 0.12, 0.37, 1.1, 3.3, 10, and 30 µg/ml in PBS.

Next, 1 µl (2 µg/ml of the solution (HT-CNB suspension) comprising the polymer particle on which the histidine-tagged protein is fixed, which was prepared in Example 1, was mixed with 39 µl of PBS comprising the histidine-tagged protein at different concentrations. The mixed solution was distributed in a 96-well plate (40 µl/well). One end of the immunochromatography strip on which the anti-histidine-tag polyclonal antibody is spotted, prepared in Example <2-1>, was dipped in the solution so as to let the solution spread on the strip. Then, the strength of each spot according to the concentrations of the sample was measured.

FIG. 3 presents the result of immunochromatography performed with changing the concentration of the histidine-tagged protein included in PBS from 0.12 µg/ml to 30 µg/ml. As the concentration of the histidine-tagged protein included in the solution increased, the color strength decreased because the pure histidine-tagged protein included in the solution competed with the histidine-tagged protein fixed on the polymer particle for the antibody conjugation with the anti-histidine-tag antibody (FIG. 3A).

On the contrary, as the concentration of the histidine-tagged protein included in the solution increased, the color strength on the spot where the anti-BSA antibody was loaded became stronger, suggesting that the polymer particles that had failed to be conjugated with the anti-histidine-tag antibody on the strip, because of the competition with the histidine-tagged protein included in the solution, was conjugated instead to the region where the anti-BSA antibody was loaded, which confirmed that the experiment was performed successfully.

As shown in FIG. 3B, a standard graph was made from the analysis of the concentration-dependent color strength. The color strength was reduced according to the concentration of the histidine-tagged protein included in the sample with presenting high correlation coefficient ($R^2=0.9982$).

EXAMPLE 3

Detection and Quantification of the Histidine-Tagged Protein Included in the Cell Extract To confirm whether or not the detection or quantification of the histidine-tagged protein included in the real cell extract was possible by immunochromatography using the polymer particle having histidine-tag fixed thereon, immunochromatography was performed with the mixture of *E. coli* extract and the histidine-tagged protein (ATG-8).

Particularly, 30 μg/ml of the histidine-tagged protein (ATG-8) was added to 1% *E. coli* extract (Sigma-Aldrich, USA). 30 μg/ml of the histidine-tagged protein (ATG-8) was three-fold diluted serially to make each final concentration of 0.12, 0.37, 1.1, 3.3, 10, and 30 μg/ml in *E. coli* extract.

Then, immunochromatography was performed by the same manner as described in Example <2-2>. When all the samples were expanded, the strength of each spot according to the concentrations of the sample was measured.

As a result, as shown in FIG. 4A, as the concentration of the histidine-tagged protein in the *E. coli* extract increased, the color strength on the spot where the anti-histidine-tag antibody was loaded decreased. On the other hand, the color strength on the spot where the anti-BSA antibody was loaded increased. The above results were consistent with the results of Example 3, which are the changes of color strength according to the concentration. That is, as the concentration of the histidine-tagged protein included in the sample increased, the color strength decreased because of the competition between the histidine-tagged protein in the solution and the histidine-tagged protein fixed on the polymer particle.

As shown in FIG. 4B, a standard graph was made from the analysis of the concentration-dependent color strength. The color strength was reduced according to the concentration of the histidine-tagged protein included in the sample with presenting high correlation coefficient ($R^2=0.9906$).

The response value corresponding to the concentration was similar to that of the pure histidine-tagged protein in Example 2. As shown in FIG. 5, compared with the response value of the pure histidine-tagged protein of Example 2, the slope was 1.1418, which was close to 1.

EXAMPLE 4

Confirmation of the Possibility of Detection of a Protein Comprising Other Histidine-Tags To investigate whether or not the detection or quantification of a recombinant protein comprising histidine-tag is possible by the immunochromatography method using the polymer particle having histidine-tag fixed thereon of the present invention, immunochromatography was performed with the sample added with fructose bisphosphate aldolase (FBA; Cusabio, USA) comprising histidine-tag and carbonic anhydrase I (CA-I, FBA; Cusabio, USA) comprising histidine-tag.

Particularly, FBA and CA-I were diluted in PBS by the same manner as described in Example <2-2> to make the final concentrations of 0.12, 0.37, 1.1, 3.3, 10, and 30 μg/ml. Then, immunochromatography was performed by the same manner as described in Example <2-2>. When all the samples were expanded, the strength of each spot according to the concentrations of the sample was measured.

As a result, the color strength decreased on the spot where the anti-histidine-tag antibody was spotted according to the concentrations of FBA and CA-I. The concentration of the histidine-tagged protein included in the sample was measured using the standard curve and function in FIG. 5, and the results are shown in Table 1.

TABLE 1

| Protein (μg/mL) | Carbonic Anhydrase I (26.3 kDa) | | Fructose bisphosphate Aldolase A (39.4 kDa) | |
|---|---|---|---|---|
| | Calculated concentration (μg/mL) | Recovery | Calculated concentration (μg/mL) | Recovery |
| 0.12 | $4.5 \times 10^{-5}$ | $3.7 \times 10^{-5}$ | — | — |
| 0.37 | 0.19 | 0.50 | 0.056 | 0.15 |
| 1.1 | 0.53 | 0.48 | 0.14 | 0.13 |
| 3.3 | 0.69 | 0.27 | 0.51 | 0.15 |
| 10 | 1.93 | 0.19 | 1.81 | 0.18 |
| 30 | 15.5 | 0.51 | 11.7 | 0.39 |

As shown in Table 1, the concentrations of FBA and CA-I actually added were different, but the reaction was equally FBA and CA-I dose-dependent. It was thus confirmed that the immunochromatography using the polymer particle of the present invention was useful not only for the detection of the histidine-tagged protein but also for the quantification of the protein included in a sample.

Therefore, the immunochromatography realized in this invention is applicable to the various proteins comprising different histidine-tags, and this method is efficient in the fast detection of a protein comprising histidine-tag (recombinant protein) only with the anti-histidine-tag antibody without any other specific antibodies specific to a target and also in the easy but accurate quantification of a protein comprising histidine-tag included in a sample without using any additional device.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. An immunochromatography kit for the detection or quantification of a histidine-tagged target protein, the kit comprising:
(a) a nanoparticle, the nanoparticle having a histidine-tag and BSA fixed thereon, and
(b) an immunochromatography strip comprising a sample pad to receive a liquid sample, the liquid sample comprising the histidine-tagged target protein,
a measurement pad, and
an absorption pad to absorb the liquid sample via capillary action;
wherein the measurement pad consists of a single test spot on which an anti-his-tag antibody is spotted to detect or quantify a histidine-tagged target protein, wherein the histidine-tag on the nanoparticle binds to the anti-his-tag antibody on the test spot competitively with the histidine-tagged target protein; and a control spot on which an anti-BSA antibody is spotted to check reaction error, wherein the BSA on the nanoparticle, which does not bind to anti-his-tag antibody competitively with the histidine tagged target protein, binds to the anti-BSA antibody on the control spot,
and wherein binding of the nanoparticle to the anti-his-tag antibody or anti-BSA antibody produces color.

2. The immunochromatography kit according to claim 1, wherein the histidine-tag fixed on the nanoparticle comprises SEQ ID NO 1 or SEQ ID NO 2.

3. The immunochromatography kit according to claim 1, wherein a size of the nanoparticle is 50 to 400 nm.

4. The immunochromatography kit according to claim 1 wherein the sample containing the histidine-tagged target protein is a cell extract.

5. The immunochromatography kit according to claim 1, wherein the nanoparticle is a polymer particle or a metal particle, wherein the metal particle is selected form the group consisting of gold, silver and white gold.

6. The immunochromatography kit according to claim 5, wherein the polymer particle is a cellulose nanobead.

7. A method for detection or quantification of a histidine-tagged target protein, said method comprising the steps of:
(a) providing the immunochromatography kit according to claim 1;
(b) mixing the nanoparticle having a histidine-tag and BSA fixed thereon with a sample containing the histidine-tagged target protein to form a mixture;
(c) and performing immunochromatography to detect or quantify the histidine-tagged target protein in the sample by adding the mixture to the sample pad of the immunochromatography strip and detecting the histidine-tagged target protein by observing color development resulting from conjugation reaction between the nanoparticle and the anti-his-tag antibody on the test spot of the measurement pad.

8. The method according to claim 7, wherein the histidine-tag fixed on the nanoparticle comprises SEQ ID NO 1 or SEQ ID NO 2.

9. The method according to claim 7, wherein the nanoparticle is a polymer particle or a metal particle, the metal particle selected from group consisting of gold, silver and white gold.

10. The method according to claim 9, wherein the polymer particle is a cellulose nanobead.

11. The method according to claim 7, wherein a size of the nanoparticle is 50 to 400 nm.

12. The method according to claim 7, wherein the histidine-tag fixed on the nanoparticle competes with the histidine-tagged target protein present in the sample.

13. The method according to claim 7, wherein the sample containing the histidine-tagged target protein is a cell extract.

14. The method according to claim 7, wherein at step (c), if the histidine-tagged target protein is present in the sample, conjugation reaction between the histidine-tag fixed on the nanoparticle and the anti-his-tag antibody on the test spot of the measurement pad decreases, resulting in a decreased color development, and if the histidine-tagged target protein is not present in the sample, the conjugation reaction between the histidine-tag fixed on the nanoparticle and the anti-his-tag antibody at the test spot of the measurement pad increases, resulting in increased color development.

15. The method according to claim 7, wherein at step (c), as concentration of the histidine-tagged target protein in the sample increases, conjugation reaction between the histidine-tag fixed on the nanoparticle and the anti-his-tag antibody at the test spot of the measurement pad decreases, resulting in decreased color development, and as the concentration of the histidine-tagged target protein in the sample decreases, conjugation reaction between the histidine-tag fixed on the nanoparticle and the anti-his-tag antibody at the test spot of the measurement pad increases, resulting in increased color development.

16. The method according to claim 7, wherein at step (c), the quantity of histidine-tagged target protein is determined by comparing the observed color development to a standard curve.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Poly-HIS Tag Sequence

<400> SEQUENCE: 1

His His His His His
1               5

<210> SEQ ID NO 2
<211> LENGTH: 6
<212> TYPE: PRT
<213> ORGANISM: Artificial Sequence
<220> FEATURE:
<223> OTHER INFORMATION: Poly-His Tag Sequence

<400> SEQUENCE: 2

His His His His His His
1               5